United States Patent [19]
Miller et al.

[11] Patent Number: 5,435,979
[45] Date of Patent: Jul. 25, 1995

[54] TOOL SUPPORT AND PRESENTATION DEVICE

[76] Inventors: Charles E. Miller, 974 Mader SE., Salem, Oreg. 97302; Eugene F. Bowlin, Jr., 2925 Comice Dr., Medford, Oreg. 97504

[21] Appl. No.: 307,930

[22] Filed: Sep. 16, 1994

[51] Int. Cl.⁶ .................... A61L 2/06; B65D 83/00; A47F 1/04; A61B 19/02
[52] U.S. Cl. ..................... 422/300; 206/44.12; 206/369; 433/77; 211/60.1; 211/69; 312/209
[58] Field of Search ................ 422/292, 300; 221/69; 206/44.12, 63.5, 368, 369; 433/77; 211/60.1, 69, 69.1, 59.2; 312/319.1, 209

[56] References Cited

U.S. PATENT DOCUMENTS

| | | | |
|---|---|---|---|
| 1,101,380 | 6/1914 | Allen | 206/44.12 |
| 1,121,934 | 12/1914 | Miller | 206/369 |
| 1,135,625 | 4/1915 | Savin | 206/369 |
| 1,357,063 | 10/1920 | Korb | 206/369 |
| 1,437,596 | 12/1922 | Korb | 206/369 |
| 1,446,921 | 2/1923 | Montag | 206/369 |
| 2,131,807 | 10/1938 | Jerum | 206/369 X |
| 2,978,110 | 4/1961 | Haskins | 206/369 X |
| 3,072,244 | 1/1963 | Smith | 206/379 |
| 4,327,060 | 4/1982 | Nisii | 422/300 |
| 4,773,544 | 9/1988 | McCarthy | 211/69.1 |
| 5,071,346 | 12/1991 | Domaas | 422/300 X |
| 5,172,810 | 12/1992 | Brewer | 422/300 X |

*Primary Examiner*—Robert J. Warden
*Assistant Examiner*—E. Leigh Dawson
*Attorney, Agent, or Firm*—Kolisch Hartwell Dickinson McCormack & Heuser

[57] ABSTRACT

A tool support and presentation device is described. The device has a base with a centrally mounted spindle and a resilient diaphragm mounted on the spindle. The diaphragm has plural collets therein and each collet may receive a tool. The diaphragm may be automatically or manually flexed to display the tools in an easily accessible configuration. In a preferred embodiment, the device is cylindrical and the diaphragm is automatically flexed by a spring disposed between the diaphragm and the base which upwardly urges a central portion of the diaphragm and thereby presents the tools in a frustoconical array.

20 Claims, 3 Drawing Sheets

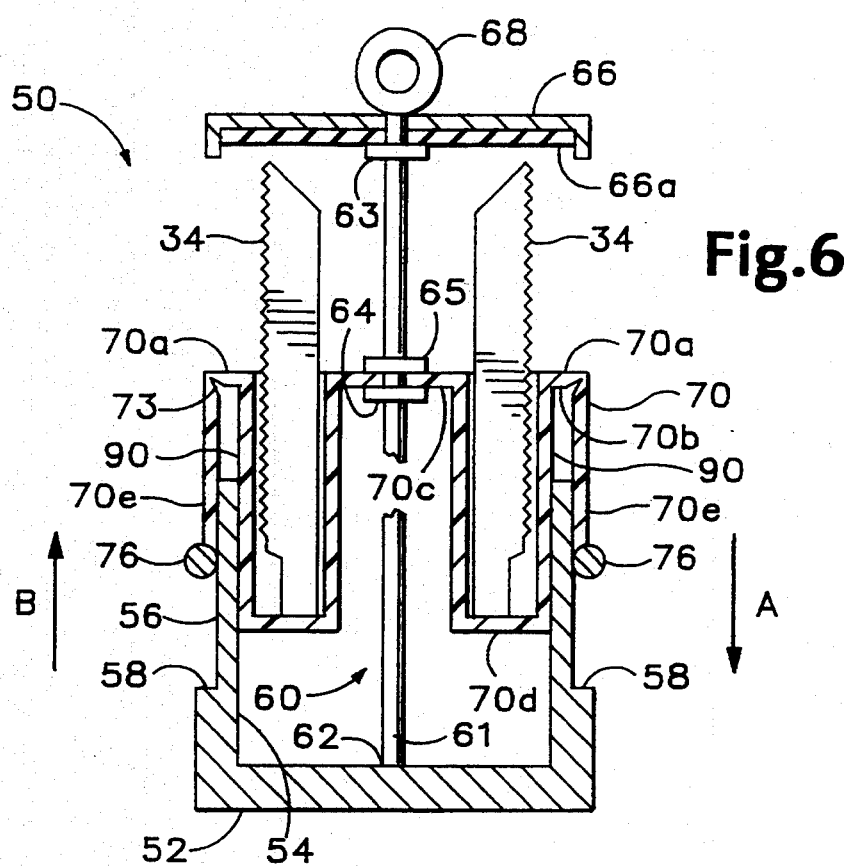
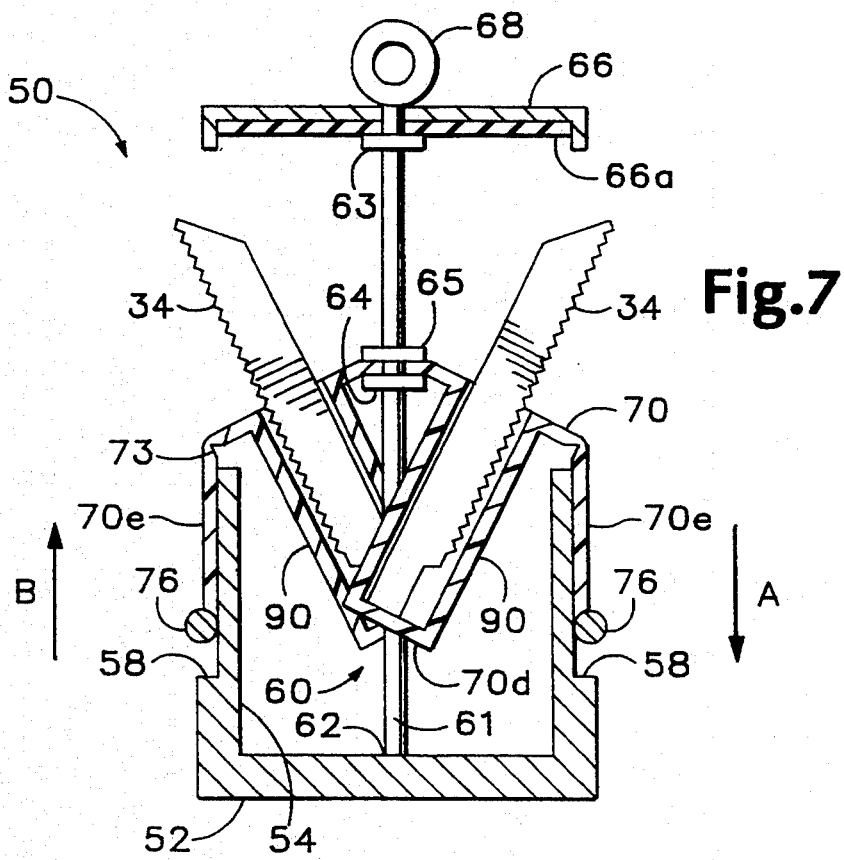

TOOL SUPPORT AND PRESENTATION DEVICE

BACKGROUND AND SUMMARY OF THE INVENTION

The present invention relates generally to support devices for elongate tools or tool heads such as the small burs used by dentists. More specifically, the invention concerns such a device that, when lidded, protectively supports the tools and optionally permits sterilized cleaning thereof and, when unlidded, presents the tools for easy removal by popping open and splaying the tools in a frustoconical array. The invention will be described in a preferred embodiment to be particularly useful with tools such as dental burs.

Dental burs are tiny drill or auger bits which are used by dentists in combination with high speed drills to administer dental procedures. These procedures include the drilling and filling of cavities resulting from tooth decay. The burs are very small and they come in many shapes. For instance, to enable a dentist to perform intricate site-specific excavation, a minute drill point may be required. Alternatively, to perform relative large-scale excavation, a larger point or drill tip may be required.

Typically, these burs are characterized as having cylindrical bottom portions. The cylindrical bottoms are usually received in and fixedly secured in the drill's chuck. Thereafter, various drilling procedures may be undertaken. Because a dentist may require a number of different burs during any one procedure, it is desirable to store the burs in a central location, such as a bur holder. It is also desirable to be able to conveniently and easily access the burs throughout the administration of a dental procedure. It is of paramount importance that the burs remain in a clean, sterilized condition. Having many densely packed burs in a holder increases the chances that a bur will be inadvertently contacted and thereby contaminated.

Thus, it is desirable to have a device which centrally holds or stores dental burs and presents them, on demand, in a fashion which greatly reduces the chances of inadvertent contamination and facilitates their extraction from the holder.

Conventional tool support devices may be characterized as follows. U.S. Pat. No. 4,327,060, entitled "STERILIZING-CONTAINING DEVICE FOR DENTAL TOOLS" issued to Nisii, discloses an open top container for receiving a dental tool support in the form of an open-bottom cylinder provided with threads around its upper and lower ends which are engaged in threads in the upper end of the container. The open-bottom cylinder is provided with plural bores into which various dental burs are received. The burs are received such that their top portions, or drill heads, remain within the container, in a substantially vertical orientation relative to the base of the container. Removing the burs from the container is complicated by the fact that only a short portion of each bur's cylindrical shaft rises above the cylinder. This is undesirable because the burs are presented for removal in a crowded configuration. Moreover, only a small portion of each entire bur is presented for removal. This is undesirable because, while one bur is removed, another adjacent bur may be inadvertently plucked thereby increasing the chances of, among other things, contamination.

U.S. Pat. No. 2,978,110 entitled "RACK-LIKE HOLDER FOR SMALL ARTICLES" issued to Haskins discloses a case with a hemispherical holder body for holding articles such as dental drills. Specifically, Haskins discloses a cylindrical holder having a base, a cover, and a holder body disposed within the base having plural fingers for holding articles such as dental drills, pencils, lipsticks, and spools of thread. The body may be flexed inwardly or outwardly after the manner of a diaphragm. Centrally disposed on the holder is a stem which extends upwardly. When the cover is closed, the holder is collapsed within the base with a bottom portion thereof resting on the base. When the cover is removed, the stem may be grasped by the user and the holder pulled upwardly to extend it outwardly from the base wherein the articles held in the fingers are exposed and accessible.

Haskins discloses, in one embodiment (see FIG. 5), a coil spring interposed between the base and the holder to prevent the diaphragm from resting on the base due to the weight of articles held in the fingers. The holder in Haskins does not automatically present the tools upon removal of the container's cover. Rather, the user must physically grasp the stem on the holder and pull the stem upwardly to present the tools. The tools are thereafter presented in a substantially vertical orientation relative to the base. By having to reach into the holder to extract held tools, the chances of contamination are greatly increased. Further, when the tools are in the stored position within the container (see FIG. 1), the respective weights thereof tend to draw the top portions of the tools toward the center where they may inadvertently contact one another.

To minimize the risk of contaminating the tools following sterilization, and, to facilitate the extraction thereof, it is desirable to have the tools automatically presented in an outwardly arrayed or frustoconical manner. Neither Nisii nor Haskins provides for the tools to be automatically presented in a splayed manner or frustoconical array. Rather, both display or present the tools in a vertically orientation relative to the base with either the tool heads or tails in close proximity. This is inconvenient and increases the chances of inadvertently touching thereby contaminating adjacent tools.

Moreover, the holder disclosed in Haskins is a solid disc-like structure with no provisions to promote the relative independent movement of the held tools. It is desirable that the held tools be able to move relatively independent of one another in their held positions to decrease the chances of one tool inadvertently contaminating another tool or accidentally puncturing a dentist's glove. Without relative independent movement between adjacent tools, when one tool is removed, any downward force perpendicular to the diaphragm plane, such as that caused by the dentist's hand, will cause other adjacently held tools to be drawn toward the point of application of the force.

Further, when sterilizing held tools such as dental burs, it is necessary that all portions of the bur, specifically the bottom held portions be sterilized otherwise there is a risk that all of the burs will be contaminated. The fingers disclosed in Haskins into which the bottom portions of the articles, i.e. dental burs are held, provide for a firm, flush fit such that if the held articles were to be sterilized or cleansed, the bottom portions thereof would remain unsterilized.

With these problems in mind, it is an object of this invention to provide a device to hold and support plural tiny tools, such as dental burs, and to present the tools, upon demand, in an arrangement providing convenient access to the user and reducing the chances of inadvertent contamination. Such a device will have a flexible diaphragm with characteristics enabling it to change its shape to effect the presentation of held tools.

It is another object of this invention to employ the use of a diaphragm to hold tiny tools, wherein the diaphragm employs a construction to promote the relative independent movement of the held tools. The relative independent movement of the tools while in their held position greatly reduces the chances that adjacent tools may contact one another or be drawn toward a user's hand when a tool is removed.

It is another object of this invention to provide a device to hold and support plural tiny tools (such as dental drill bits) while they are being sterilized and cleaned. Such a device will have holders or collets for receiving and holding each tool, and each collet will have a cross-section which allows for the entire tool, specifically the bottom portions, to be sterilized.

It is yet another object of this invention to provide a device to hold, support and present plural tiny tools, which device may be operated using only one hand. Such a device will enhance greatly the convenience with which tools may be inserted and extracted, or loaded and used.

It is a further object of the invention to provide a device for holding and displaying tools which has a reduced height so that such device is more compatible with sterilization and other procedures.

In summary, the invention in its preferred embodiment achieves these and other objects in the form of a tool support and presentation device having a circular base with a central, vertical spindle extending upwardly and a circular or disk-shaped cover with a central, cylindrical barrel designed to mate with the base's spindle. Within the base and extending around the bottom of the spindle is a coil spring. The spring presses upwardly against a flexible, resilient circular disc. This circular disc has flanges that are tucked under the shoulder on the top edge of the base. Collets of square cross section are held within holes in each flange, and each collet holds one tiny tool.

When the cover is removed, the spring urges the resilient circular disc upwardly and the tiny tools splay out to allow easy digital access to each of them. The cover presses the spring down when it is mounted on the vertical spindle, which has a locking protuberance for mating with a slotted key-hole structure in the cover's barrel. When the cover is in place, the tools move to a substantially vertical orientation and the cover prevents them from escaping from the device, despite vibration and movement within their collets. When the device is closed the tools may be cleaned using autoclaving, ultrasonic or other cleaning techniques. During autoclaving, the square cross section collets provide clearance and support for the complete cleaning of the tools, which have substantially cylindrical shafts. Tiny cylindrical tools can be cleaned more efficiently and effectively when held in a collet having a square cross section.

In one embodiment, a hand-held device is provided with a cylindrical base having upwardly extending walls defining an opening, an upwardly extending spindle joined to the base, and a cylindrical cover mounted to the upper end of the spindle. The walls include a recessed portion defining an annular shoulder. A resilient diaphragm spanning the opening defined by the base's walls is fitted at its periphery with an annular ring dimensioned to fit around the base's wall, specifically the recessed portion thereof. The diaphragm is provided with apertures or collets into which tiny tools may be placed. Support structure is provided intermediate the ends of the spindle and supports the diaphragm thereby providing a surface against which the diaphragm may be bent or stretched.

When the annular ring is drawn along the base's wall in the direction of the base, the diaphragm is bent or stretched over the support and the held tools are presented in an outwardly arrayed or splayed manner. The resilience of the diaphragm causes it to rebound or assume its original shape upon cessation of the drawing action by the user. In its original shape, the diaphragm, and particularly the collets, orient the tools in a vertical upright manner. In its flexed shape, the diaphragm is bent or stretched and the tools are presented in a splayed manner.

Embodiments of the present invention may include an offset member mounted around the spindle for rotation thereabout, having radially outwardly extending selection arms or flanges. A tab connected to one of the selection arms may be shifted relative to the base, which cause the selection arms to tilt the individual collets so that the overall height of the device may be reduced.

Usually, dentists wear gloves to protect from viral transmission to/from the patient. With prior art tool support devices having the tool heads packed closely together as they exit the autoclave, often the dentist would have difficulty picking the desired tool without interfering with an adjacent tool. At worst, the glove might be pricked by a sharp adjacent tool, and the prophylactic protection of the glove compromised. With the invented tool support and presentation device, the tools automatically splay for their presentation in a configuration that, while permitting dense packing for autoclaving, yet are automatically and conveniently separated for selective use.

These and additional objects and advantages of the present invention will be more readily understood after a consideration of the drawings and the detailed description of the preferred embodiment.

BRIEF DESCRIPTION OF THE DRAWINGS

FIG. 6 is a side-plan view of an alternative embodiment of the device with portions of the device broken away to show detail.

FIG. 7 is a side-plan view of the device corresponding to FIG. 6, but showing the device with the supported tools splayed for presentation with portions of the device broken away to show detail.

DETAILED DESCRIPTION OF THE PREFERRED EMBODIMENT

Figure 1:
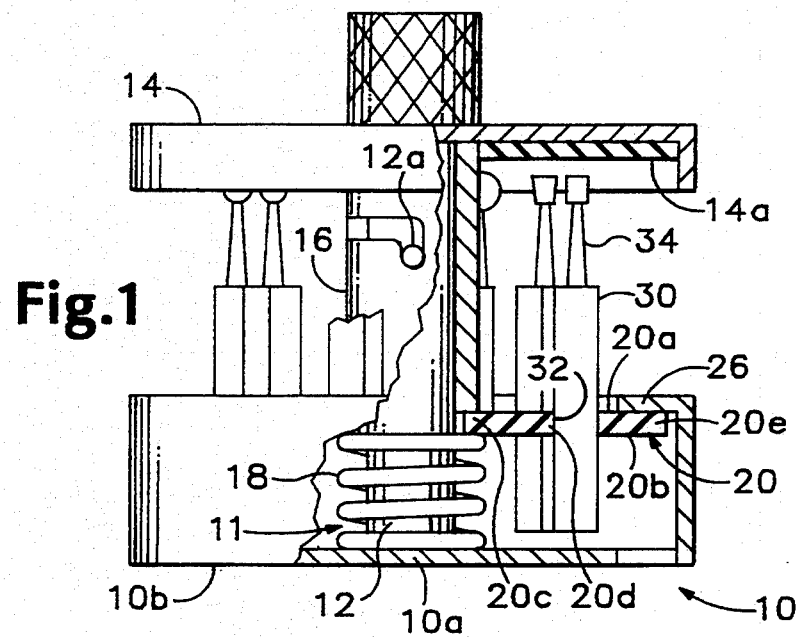
FIG. 1 is a side-plan view of the invented device shown in its lidded configuration, made in accordance with its preferred embodiment, with portions of the device broken away to show detail.
Figure 2:
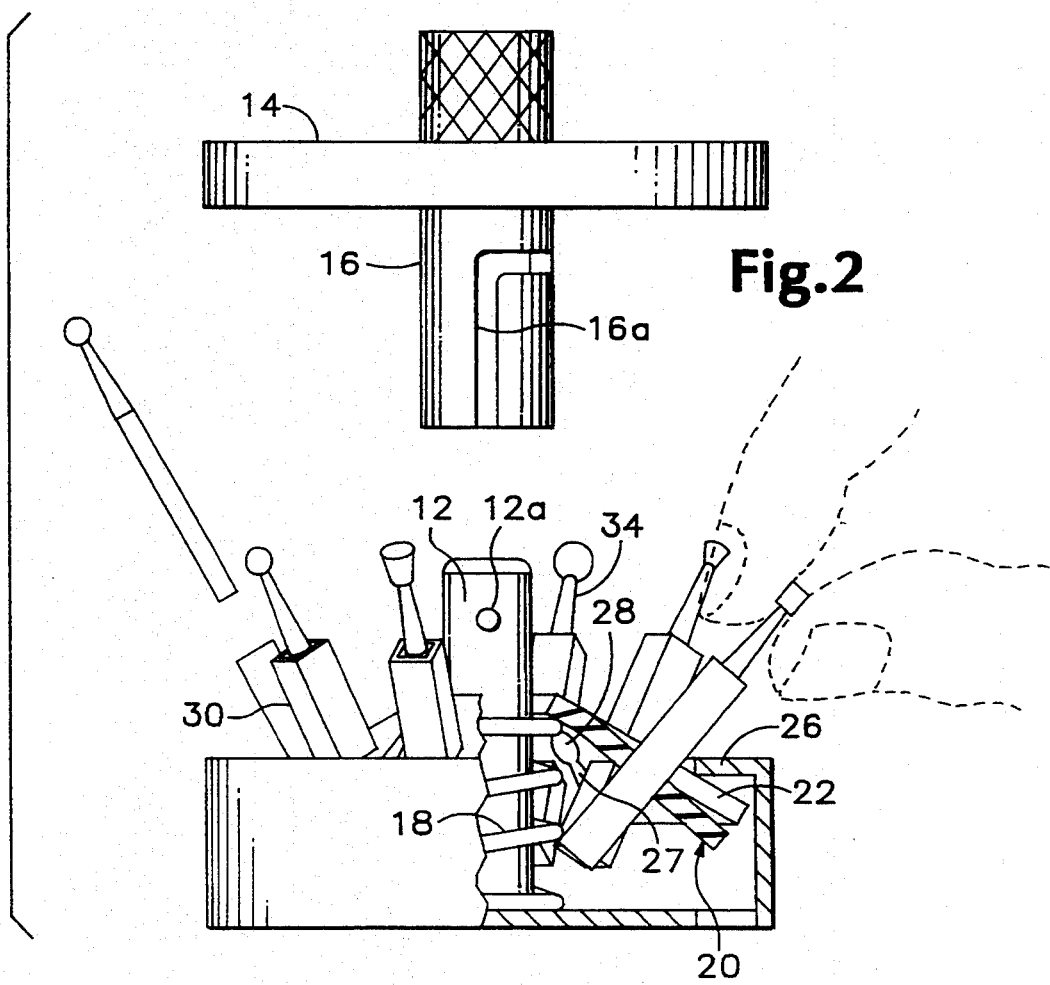
FIG. 2 is a side-plan view of the device corresponding to FIG. 1 but showing the device in its unlidded configuration with the supported tools splayed for presentation.
Figure 3:
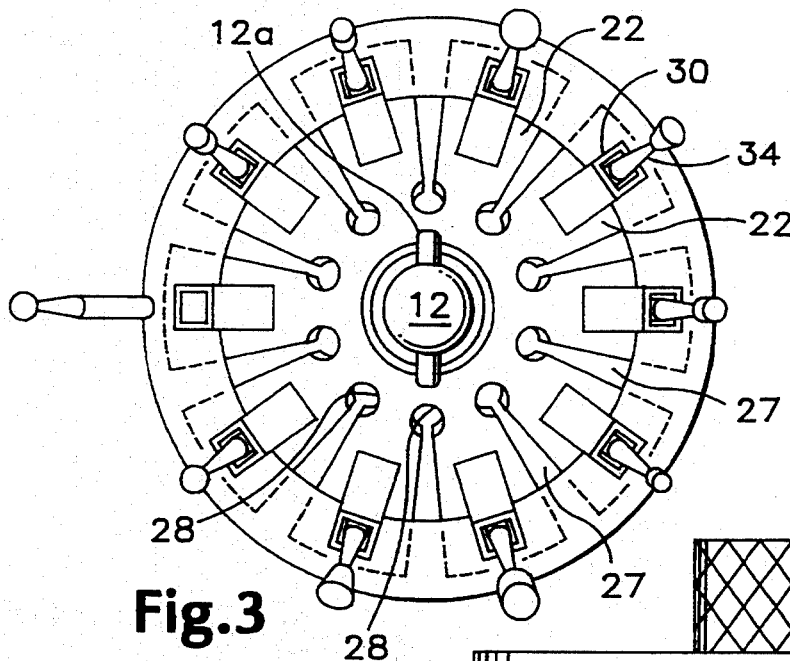
FIG. 3 is a top-plan view of the device corresponding to FIG. 2.

Referring to FIGS. 1-3, the device has a cylindrical base 10 defining a plane, and an inner member shown generally at 11. Base 10 includes a central portion 10a and an outer portion 10b. Inner member 11 in accordance with the preferred embodiment of FIGS. 1-3 includes an elongate spindle 12 mounted on central portion 10a and a coil spring 18 received by spindle 12. Cylindrical cover 14 has a centrally mounted cylindrical barrel 16 designed to mate with inner member 11, and more specifically spindle 12. Cylindrical cover 14 includes non-abrasive shock-absorbing lining 14a which both prevents the tools from escaping the device and protects them while they are held therein.

A resilient shape-retentive diaphragm 20 preferably formed from any suitable deformable material such as an elastomer, is in the form of a disc mounted on inner member 11 adjacent the base. Diaphragm 20 has an outer surface 20a, an inner surface 20b, and a central, an intermediate, and a peripheral region 20c, 20d, and 20e, respectively. When diaphragm 20 is mounted on the inner member, inner surface 20b faces the base and spring 18 presses upwardly against, or biases, diaphragm 20 at central region 20c.

Diaphragm 20 preferably includes plural flanges 22 which extend radially outwardly from central region 20c to form intermediate region 20d and peripheral region 20e. The flanges are tucked under an outer member 26, which may take the form of an inwardly projecting shoulder 26 on the top edge of base 10. Intermediate region 20d includes apertures 32 each of which receives a collet 30. Collets 30 are elongate and have square cross sections best shown in FIG. 3, which cross sections are orthogonal to the long axes of each collet. It will be appreciated that collets 30 may have other polygonal or multi-linear cross sections such as that of a triangle or pentagon. Each of the flanges is separated from the other flanges by plural cutout regions, or spaces, 27, most easily seen in FIG. 3. Pairs of adjacent spaces promote the relative independent movement of the corresponding flange by allowing each flange controllably to move up and down, and controllably to twist slightly, relative to the base without interfering with adjacent flanges. Each space 27 terminates at a radially inward extreme with hole structure 28 for further promoting such relative independent movement (and reducing the tendency of diaphragm 20 to tear).

Although the device has been described as having a cylindrical base and circular diaphragm, it will be appreciated that the base and diaphragm may come in a variety of shape and sizes. For instance, the base and diaphragm may be rectangular, triangular or other preferably regular shapes. Moreover, it is contemplated that coil spring 18 may be a leaf spring or any of a variety of springs or other biasing mechanisms capable of urging the central region of the diaphragm upward or otherwise flexing it into a convex shape.

Referring now to FIGS. 1 and 2, it may be seen that diaphragm 20 has two configurations during different phases of the operation of device 10. FIG. 1 shows diaphragm 20 in its generally planar configuration and FIG. 2 shows the diaphragm in its arcuately flexed configuration.

In its planar configuration (see FIG. 1), the surface of diaphragm 20 lies in a plane generally parallel to the plane defined by base 10 and collets 30 extend generally orthogonal to the plane defined by the base, i.e. they are orientated substantially vertically when the base is on a horizontal support surface. Put another way, in the planar configuration of diaphragm 20, planes transversing each collet orthogonal to the long axis thereof are substantially parallel to the plane defined by the base.

In its flexed configuration (see FIG. 2), diaphragm 20 is flexed convexly away from the base such that planes transversing each of the collets orthogonal to the long axes thereof are relatively angularly offset from the plane defined by the base. This orients collets 30 and the tools held therein in a frustoconical array.

When cover 14 is removed, the disc assumes its flexed configuration as spring 18 urges the central region of diaphragm 20 upwardly and tiny tools 34 splay out frustoconically to allow easy access to each of them. Barrel 16 on cover 14 counteracts the upward force of spring 18 and presses diaphragm 20 into its planar configuration when the cover is mounted on spindle 12. Spindle 12 has a locking protuberance 12a for mating, when so mounted, with slotted key-hole structure 16a in the cover's barrel. When the cover is in place, tools 34 are in a substantially vertical orientation relative to the horizontal base, such as that shown in FIG. 1, and cover 14 prevents them from escaping from the device. The tools may vibrate and move slightly within their collets, but they will not escape the device.

When device 10 is closed, the tools may be cleaned using autoclaving, ultrasonic or other cleaning equipment. During autoclaving, the square cross section of the collets provides clearance and support for the complete cleaning of the tools, which have substantially cylindrical shafts. Tiny cylindrical tools may be cleaned more efficiently and effectively when held in a collet of square cross section. The corners of the collets provide for the release of contaminants and the flow of fluids due to their non-conforming cross sections relative to the cross section of the held tools. As discussed above, the importance with regard to the square cross section is that each tool is free, to some degree, to move within the collet thereby facilitating cleaning thereof. While collets having square cross sections are particularly preferred, those of skill will appreciate that the use of collets of any useful cross section, including a round one, are within the spirit and scope of the invention.

Figure 4:
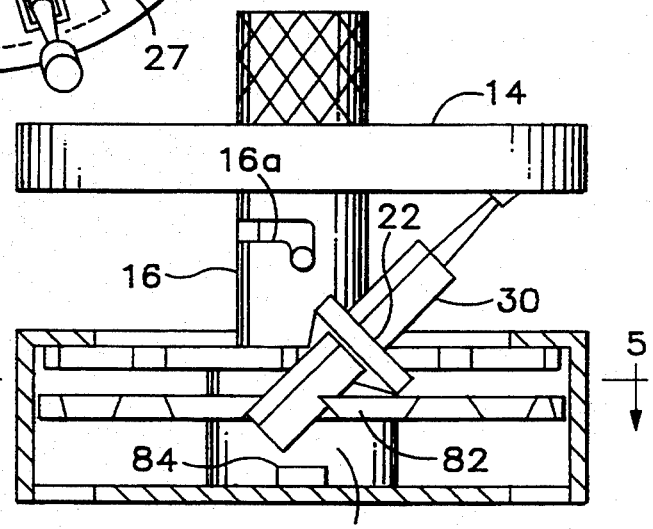
FIG. 4 is a side-plan view of an alternative embodiment of the device with portions of the device broken away to show detail.
Figure 5:
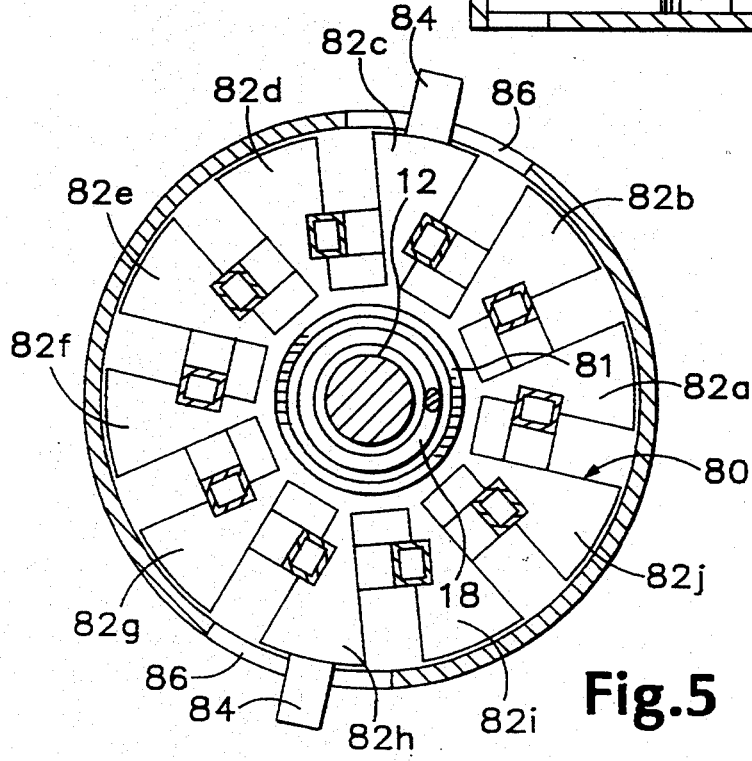
FIG. 5 is a top-plan view of the device corresponding to FIG. 4 along lines 5—5 showing the device with the supported tools tilted therein.

Referring now to FIGS. 4 and 5, an adaptation of the preferred embodiment of FIGS. 1-3 which will reduce the overall height of the device may be seen as an offset member indicated generally at 80. Offset member 80 is mounted on spindle 12 for rotation thereabout. Member 80 has plural selection arms 82a, 82b, 82c, 82d, 82e, 82f, 82g, 82h, 82i, and 82j, referred to collectively as selection arms 82 which selection arms are adjacent each collet. Selection arms 82 extend radially from a central hub 81. Further, a tab 84 is provided either on one of the selection arms or attached to hub 81 and extends outwardly through a tab slot 86 in base 10. Tab 84 may be moved arcuately within tab slot 86 thereby rotating offset member 80 about the spindle such that each of the selection arms 82 tilts a corresponding one of the collets such that planes transversing each of the collets orthogonal to the long axes thereof are relatively angularly offset from the plane defined by the base. By tilting the collets in this way, the overall height of the device is reduced making it more compatible with sterilization and other logistic procedures.

Usually, dentists wear gloves to protect from vital transmission to/from the patient. With prior art tool support devices having the tool heads packed closely together as they exit the autoclave, often the dentist would have difficulty picking the desired tool without interfering with an adjacent tool. At worst, the glove might be pricked by a sharp adjacent tool, and the prophylactic protection of the glove will have been compromised. With the invented tool support and presentation device, the tools semi-automatically splay for their presentation in a configuration that, while permitting dense packing for autoclaving, yet are semi-automatically and conveniently separated for use.

Moreover, the individual tools are located each on a flange which underlaps a shoulder portion of the base. These flanges are provided with apertures in which the collets are received. Thus, a tiny tool may be placed in each collet and held for cleaning or storing. Separating each flange is a space terminating in hole structure located near a central portion of the diaphragm. These spaces and hole structure promote the relative independent free movement of each flange by allowing each flange to move up and down and slightly to twist, relative to other adjacent flanges without interfering with them.

Thus, a person desiring to insert or remove a tiny tool from the collet need only remove the cover, whereupon the central region of the diaphragm is automatically urged upwardly relative to the base, presenting the collets or tools in an outwardly arrayed manner. Thereafter, the user may conveniently pluck or insert a tool from or into the frustoconically arrayed collets. The spaces between the plural flanges allow each flange to move relatively independently of one another with the result that when a user, e.g. a dentist, attempts to remove or insert a tool into the collet, any inadvertent downward or lateral force, such as in a direction perpendicular to the diaphragm or on the collet itself, will cause only the flange in which the collet is located to bend downwardly. Adjacent flanges will remain substantially in place and will not be drawn toward the direction of the applied force, as would be the case if there were no spaces between the flanges.

After the desired tool has been inserted into or removed from the collet, the cover may be replaced which brings the tools to a substantially vertical orientation for easy storing. In their stored positions, the tools are held protectively in place by the cover which also prevents the tools from falling out if the device were to be inverted.

An alternative embodiment, also known as a hand-held embodiment, is shown in FIGS. 6 and 7, generally at 50. Preferably right cylindrical device 50 may be seen to include a cylindrical base 52 defining a plane, which base has an upwardly extending wall portion 54 defining an opening. Wall portion 54 includes a recessed portion 56, forming an annular shoulder 58. Like the preferred embodiment described above, device 50 has an inner member 60 that is centrally mounted on base 52 and may be seen to include a spindle 61 and an annular support 64. Spindle 61 has first and second ends, 62 and 63 respectively, with first end 62 joined to the base at a central region thereof. Second end 63 is joined to cylindrical cover 66 which cover may be provided with a lanyard loop 68 for attaching device 50 to a key ring or belt (not shown). Cover 66 includes a non-abrasive shock-absorbing lining 66a which both prevents the tools from escaping the device and protects them while they are held therein. Support 64 is fixedly mounted on spindle 61, intermediate first and second ends 62 and 63 respectively.

Mounted on base 52 and spanning the opening defined by upwardly extending wall portion 54 is a resilient shape-retentive diaphragm 70. The diaphragm has inner and outer surfaces 70a and 70b respectively and a central region 70c, an intermediate region 70d and a peripheral region 70e. Diaphragm 70 is provided with integrally formed collets 90 in the intermediate region 70d.

An annular ring 76, having a diameter slightly larger than the diameter of recessed wall portion 56, is disposed around that portion and joined to diaphragm 70 at peripheral region 70e. As a result, the combination of diaphragm 70 and ring 76, (which may be formed integrally therewith) when drawn along recessed wall portion 56 toward base 52 in the direction of Arrow A, causes diaphragm 70 to bend, thereby splaying tools 34 in a radially outward direction relative to inner member 60. Upon cessation of the drawing action, tools 34 are returned to their original vertical orientation by the resilient rebounding of peripheral region 70e of diaphragm 70 in the direction of Arrow B and by the return of tool-holding intermediate region 70d to the generally horizontal orientation shown in FIG. 6.

The bending or stretching of the diaphragm is enhanced by annular support 64 and opposed annular clamping member 65. Annular support 64 biases central region 70c upward in relation to a generally opposing force when ring 76 and diaphragm 70 are drawn along wall portion 56. Clamping member 65 captures central region 70c of diaphragm 70 between annular support 64 and holds central region 70c firmly in place. When a force in a direction normal to the plane defined by base 52 and toward the base is manually applied to ring 76, annular support 64 opposingly biases central region 70c causing the diaphragm to bend, thereby splaying the held tools. Diaphragm 70 is held in place during this operation by clamping member 65. An annular groove 73 in the form of a strain break or relief is provided to promote localized controlled bending and corner formation.

The hand-held embodiment works along the same principles as the preferred embodiment of FIGS. 1–3 described hereinabove. That is, a user may present the held tools in an outwardly splayed manner to facilitate removal and replacement from or within a collet. Holding the device in the palm of one's hand, with the base resting flush thereon, the thumb and index finger may reach up and engage the annular ring to which the peripheral region of the diaphragm is joined. By pulling downwardly in the direction of the base, the user exerts a force which bends the diaphragm downwardly outwardly from the annular support disposed on the device's spindle, thereby causing one or more held tools to splay outwardly for easy access.

Thus a new and innovative design in a tool support and presentation device has been disclosed which will both hold tiny tools and present them, upon demand, in an easily accessible configuration. The structure includes a base having a centrally mounted spindle and a resilient diaphragm mounted on the spindle, the diaphragm having collets for holding tiny tools. The diaphragm may be either automatically or manually flexed to present the tools in an outwardly arranged or frustoconical configuration. When automatically flexed, the diaphragm is confronted by a spring therebeneath to urge a central region of the diaphragm upwardly. When manually flexed, the diaphragm may be drawn by the user along a direction toward the base where during such drawing a central region of the diaphragm is held in place relative to the spindle, which drawing causes the diaphragm to flex and thereby present the tools.

It will be appreciated that the pop-and-splay tool support and presentation device is not limited in utility to the dental field, but is useful generally in fields where relatively tiny, plural tools might be closely configured and secured for cleaning and/or storage and yet presented accessibly and perhaps better splayed in preparation for or in connection with their use.

While the present invention has been shown and described with reference to the foregoing preferred embodiment, it will be apparent to those skilled in the art that other changes in form and detail may be made therein without departing from the spirit and scope of the invention as defined in the appended claims.

We claim:

1. A device for holding and displaying tools in a radially outwardly arrayed manner, said device comprising:
    a base defining a plane, wherein said base has a central portion and an outer portion;
    an inner member disposed on said central portion of said base;
    an outer member adjacent said outer portion of and connected to said base;
    plural elongate collets;
    a resilient, shape-retentive diaphragm having an outer and an inner surface, and a central, an intermediate and a peripheral region, wherein said intermediate region includes plural apertures therethrough, wherein each of said apertures receives a collet, and wherein said diaphragm is mounted adjacent said base on said inner member with said inner surface facing said base and with said peripheral region being adjacent said outer member,
    and wherein said inner surface of said central region is confronted by said inner member for biasing said central region in a first direction generally orthogonal to such plane defined by said base,
    and further wherein said diaphragm has a generally planar configuration and a flexed configuration such that in said planar configuration, planes traversing each of said collets orthogonal to the long axes thereof are substantially parallel to such plane defined by said base, and in said flexed configuration, said diaphragm is flexed convexly away from said base such that planes traversing each of said collets orthogonal to the long axes thereof are relatively angularly offset from such plane defined by said base, and further wherein said flexed configuration is effected by a force generally opposing said biasing, said force being manipulably applied by said outer member at said peripheral region of said diaphragm.

2. The device of claim 1, wherein said base is cylindrical and said diaphragm is disc-shaped and wherein said outer member includes an inwardly projecting shoulder portion and said inner member includes an elongate spindle having radially extending protuberances, and an adjacently mounted spring, and wherein said device further includes a cylindrical cover having a centrally disposed barrel portion wherein said barrel portion includes slotted structure to lockingly mate with said protuberances.

3. The device of claim 2, wherein said diaphragm includes plural flanges extending radially outwardly from said central region forming said intermediate and peripheral regions and wherein each of said apertures is located on a flange.

4. The device of claim 3, wherein each of said flanges is separated from other adjacent flanges by spaces extending radially outwardly through said intermediate and peripheral regions, and further wherein each of said spaces includes a hole-forming structure proximate said central region.

5. The device of claim 2, wherein said collets have polygonal cross-sections.

6. The device of claim 1, wherein said base is cylindrical and said inner member includes an elongate spindle and support structure mounted thereon, wherein said support structure supports at least a portion of said diaphragm, and further wherein said outer member includes ring structure joined to said diaphragm at a peripheral region thereof.

7. The device of claim 6 further comprising a cylindrical cover mounted on said spindle.

8. The device of claim 6, wherein said collets have polygonal cross-sections.

9. The device of claim 1 further comprising an offset member mounted on said inner member for rotation thereabout, said offset member having plural selection arms adjacent said collets such that, when said offset member is rotated, said collets are tilted by said selection arms such that planes traversing each of said collets orthogonal to the long axes thereof are relatively angularly offset from such plane defined by said base.

10. The device of claim 9 wherein said selection arms extend radially outwardly from a central hub.

11. A storage and display device for elongate tools for automatically displaying stored tools in an outwardly arrayed configuration, said device comprising:
    a base defining a plane wherein said base has upwardly extending walls, said walls having an inwardly projecting shoulder portion;
    a spindle centrally disposed on said base;
    plural elongate collets;
    a resilient shape-retentive diaphragm mounted on said spindle, said diaphragm having a central, an intermediate, and a peripheral region wherein said intermediate region includes plural apertures therethrough, each aperture receiving a collet, and wherein each of said collets holds a tool in a substantially orthogonal orientation relative to said plane, and wherein said peripheral region underlaps said shoulder portion; and
    a spring adjacent said base, between said base and said diaphragm, for biasing said central region of said diaphragm away from said plane, and wherein a generally opposing force in relation to such biasing is exerted on said peripheral region by said shoulder portion thereby causing said diaphragm to be flexed convexly away from said base thereby displaying held tools in plural orientations relatively angularly offset from said plane.

12. The device of claim 11, wherein each of said collets has a polygonal cross-section.

13. The device of claim 11, wherein said base is cylindrical and said diaphragm is in the form of a disc, wherein said disc has radially outwardly extending flanges wherein said flanges extend from said central region of said disc and form said intermediate and peripheral regions, and wherein said intermediate region includes said apertures and said peripheral region underlaps said inwardly projecting shoulder portion on said base.

14. The device of claim 13, wherein each of said flanges is separated from other adjacent flanges by spaces extending radially outwardly through said intermediate and peripheral regions, and further wherein each space includes a hole-forming structure proximate said central portion.

15. The device of claim 13 further comprising a cylindrical cover having a centrally disposed barrel portion to removably receive said spindle.

16. The device of claim 15, wherein said barrel portion includes slotted structure and wherein said spindle includes protuberant structure to mate with said slotted structure when said cover is installed on said spindle, and further when so installed, said barrel portion urges said central region of said diaphragm against said spring so that said diaphragm is substantially parallel to said plane defined by said base.

17. The device of claim 11 further comprising an offset member mounted on said spindle for rotation thereabout, said member having plural selection arms adjacent said collets such that when said offset member is rotated said collets are tilted by said selection arms such that planes traversing each of said collets orthogonal to the long axes thereof are relatively angularly offset from such plane defined by said base.

18. A device for stowing and splaying tools comprising:

a base having a central portion and an outer portion and walls joined to said base at said outer portion thereof, said walls extending angularly away from said base, wherein said walls define an opening;

a spindle having a first and second end, wherein said first end is joined to said central portion of said base;

a resilient shape-retentive diaphragm spanning said opening, said diaphragm having a central, an intermediate, and a peripheral region, wherein said diaphragm is mounted on said spindle at said central region, and wherein said intermediate region includes plural collets integral therewith, wherein said collets are generally orthogonally oriented relative to said base; and an outer member adjacent said walls and joined to said peripheral region of said diaphragm, said outer member for drawing said diaphragm along said walls in a direction toward said base thereby angularly offsetting said collets from said base relative to said orthogonal orientation thereby splaying said collets.

19. The device of claim 18 further including support structure fixedly connected to said spindle between said first and second ends thereof, said support structure biasing said central region of said diaphragm away from said base relative to a generally opposing digitally applied force at said outer member.

20. The device of claim 19 wherein said base is cylindrical and said diaphragm is disc-shaped and wherein said outer member includes an annular ring having a diameter slightly larger than the diameter of said walls, such that said ring receives said walls therethrough and may be reciprocally drawn therealong, and further wherein said devices includes a clamping member connected to said spindle adjacent said diaphragm, said clamping member fixedly holding said central region of said diaphragm relative to said spindle.

* * * * *